United States Patent [19]

Hermens et al.

[11] Patent Number: 5,089,482
[45] Date of Patent: Feb. 18, 1992

[54] PHARMACEUTICAL COMPOSITIONS FOR NASAL ADMINISTRATION CONTAINING STEROID HORMONES AND DIMETHYL-β-CYCLODEXTRIN

[76] Inventors: Walter A. J. J. Hermens, Thorbeckestraat 80, 6136 DD Sittard; Franciscus W. H. M. Merkus, Mozartlaan 7, 3723 JL Bithoven, both of Netherlands

[21] Appl. No.: 372,917

[22] Filed: Jun. 28, 1989

[30] Foreign Application Priority Data

Jul. 1, 1988 [NL] Netherlands ............ 8801670

[51] Int. Cl.$^5$ ............ A61K 31/56; A61K 31/57; A61K 31/565; A61K 31/715
[52] U.S. Cl. .................. 514/58; 514/177; 514/182; 514/26; 536/103
[58] Field of Search ............ 514/182, 177, 58, 26; 536/103

[56] References Cited

U.S. PATENT DOCUMENTS

| 4,383,992 | 5/1983 | Lipari | 514/58 |
| 4,383,993 | 5/1983 | Hussain et al. | 514/177 |
| 4,596,795 | 6/1986 | Pitha | 514/58 |
| 4,642,305 | 2/1987 | Johansson et al. | 514/182 |
| 4,877,774 | 10/1989 | Pitha et al. | 514/58 |

FOREIGN PATENT DOCUMENTS

| 0254586 | 5/1963 | Australia . |
| 2839033 | 3/1980 | Fed. Rep. of Germany . |
| 58-113275 | 7/1983 | Japan . |

OTHER PUBLICATIONS

Szejtli; Chemical Abstracts 100:161740q (1984).
Szente et al.; Chemical Abstracts 103:11351m (1985).
Kumar et al.; Curr. Sci. 43:435–439 (1974).
Gopinath et al., Curr. Ther. Res. 23:596–607 (1978).
Pitha et al.; J. Pharm. Sci. 75(2):165–167 (1986).
Uekama et al.; CRC Crit. Rev. Ther. Drg. Car. Syst. 3:1–40 (1986).
Rigg et al.; J. Clin. Endocrin. Metab. 45:1261–1264 (1977).
Hermens et al.; Pharm. Res. 7(5):500–502 (1990).
Szejtli; J. of Inclusion Phenomena 1:135–150 (1983).
Szente et al.; J. of Inclusion Phenomena 2:631–636 (1984).
Muller et al.; Int. J. Pharm. 26:77–88 (1985).
Yoshida et al.; Int. J. Pharm. 46:217–222 (1988).
Hermens et al.; Pharm. Res. 4(6); 445–449 (1987).
Schipper et al.; Int. J. Pharm. 64:61–66 (1990).
Kumar et al., Nature 270:532–534 (1977).
Kumar et al.; Recent Adv. Reprod. Reg. Fertil. pp. 49–56 (1979).
Hussain et al.; J. Pharm. Sci. 70(4):466–467 (1981).
Bawarshi-Nassar et al.; Drug Metab. Dist. 17(3):248–254 (1989).

*Primary Examiner*—Ronald W. Griffin
*Assistant Examiner*—Nancy S. Carson
*Attorney, Agent, or Firm*—Cooper & Dunham

[57] ABSTRACT

Pharmaceutical compositions having a formulation and form suitable for nasal administration, and containing 17β-estradiol and/or progesterone. According to the invention, the composition also contains dimethyl-β-cyclodextrin.

30 Claims, 3 Drawing Sheets

PHARMACEUTICAL COMPOSITIONS FOR NASAL ADMINISTRATION CONTAINING STEROID HORMONES AND DIMETHYL-β-CYCLODEXTRIN

This invention relates to a pharmaceutical composition having a formulation and form suitable for nasal administration, and containing a sex hormone selected from 17β-estradiol, progesterone, and combinations thereof.

17β-estradiol is the most active natural human oestrogen. The oral administration of 17β-estradiol is accompanied by a considerable conversion into the less active hormone estrone and subsequently into other metabolites. This conversion takes place during the absorption from the intestine and transport through the liver (first pass). This requires high dosages to achieve the effects desired as compared with parenteral administration. Progesterone, too, which is the most important natural human progestagen, has a very limited activity after oral administration, by reason of the metabolism in the gastro-intestinal tract and the first-pass effect of the liver.

By reason of this limited oral effectiveness of the natural female sex hormones, synthetic derivatives have replaced the natural hormones in virtually all cases.

The synthetic derivatives, however, have an adverse stimulating effect on the protein synthesis of the liver (possibly promoting thrombosis) and exhibit a diabetogenic effect, in contrast to the natural sex hormones.

For the above reasons, there is an urgent need of suitable, non-oral compositions and dosage forms of the natural female sex hormones.

Rigg et al, J. Clin. Endocrinol. Metab. 45, 1977, pp. 1261–1264, have investigated the intravaginal and intranasal administration of 17β-estradiol in the form of a suspension in a physiological saline solution. Intranasal administration proved to be unsuitable.

In U.S. Pat. No. 4,383,993, however, intranasal administration is yet proposed for both progesterone and 17β-estradiol and esters thereof. It describes a composition for intranasal administration, comprising a solution of the sex hormones in an isotonic saline containing a surfactant, such as Tween 80, as a solubilizer. This publication shows that the sex hormones in question can be absorbed nasally, in which connection it is doubtless of importance that the hormones are offered to the nasal mucosa in a dissolved form. On account of the apolar character of the natural sex hormones, particular measures must be taken to realize the desired dissolved form, such as the use of Tween 80 or other adjuvants as solubilizers.

Adjuvants suitable for use as solubilizers, however, are often unsuitable for the nasal mucosa and/or have an insufficient solubility increasing effect. In the first case, a chronic therapy with such a composition is undesirable. In the second case, the concentration of the natural hormone in the composition is too low, so that the dosage volume must become too high to bring about an effective therapy.

It is an object of the present invention to provide a composition suitable for the nasal administration of 17β-estradiol, progesterone, or mixtures thereof, which ensures an effective absorption of the hormones, but avoids the above disadvantages of known compositions.

This object is realized, in accordance with the present invention, by providing a pharmaceutical composition of the above type which is characterized in that it also contains dimethyl-β-cyclodextrin.

For that matter, dimethyl-β-cyclodextrin is known per se from German patent application 3,118,218. In it, it is proposed for dimethyl-β-cyclodextrin to be used for the preparation of aqueous solutions of poorly soluble, biologically active, organic compounds, such as various vitamins, steroids, protanoids, local anaesthetics, etc. The combination of such substances, which include, for example, progesterone, with dimethyl-β-cyclodextrin results in the formation of intercalation complexes which are soluble in water. Generally speaking, that publication describes pharmaceutical compositions for oral or parenteral administration. Concretely, however, the publication does show infusion and injection solutions of various biologically active compounds, but pharmaceutical compositions with a formulation and form suitable for nasal administration are neither mentioned nor illustrated, let alone such pharmaceutical compositions specifically containing a sex hormone selected from 17β-estradiol, progesterone, and combinations thereof.

The ideas laid down in the German patent application have not found practical application, as will become apparent from the following publications, which point in a different direction.

In European patent application 0,149,197, attention is directed to major drawbacks reported to be involved in the use of dimethyl-β-cyclodextrin. Specifically, the application refers in this connection to a hemolytic effect and an irritant effect on mucosa and eyes, a higher acute intravenous toxicity than non-substituted β-cyclodextrin, and practical problems in connection with sterilization. Indeed, the publication recommends using a partially etherified β-cyclodextrin containing hydroxyalkyl groups.

For that matter, the objections raised in European patent application 0,149,197 against the use of dimethyl-β-cyclodextrins have not been noted with pharmaceutical compositions according to the present invention. Evidently, the concentrations to be used are so low that no trace of irritation of mucosa is found. Tests for the in vitro examination of the effect of compositions according to this invention on the ciliary movement of human nasal ciliary epithelium showed that, unlike Tween 80 containing compositions as disclosed in U.S. Pat. No. 4,383,993, they do not stop ciliary movement and are not harmful (see FIG. 1).

In addition it is surprising that the pharmaceutical compositions according to the invention result in a biological availability substantially equal to that achieved with intravenous administration. In fact, U.S. Pat. No. 4,596,795 teaches that the use of the dimethyl-β-cyclodextrin in sex hormone compositions for sublingual and buccal administration has virtually no effect on the absorption of the sex hormones, unlike poly-β-cyclodextrin and hydroxypropyl-β-cyclodextrin. That publication, too, therefore, teaches away from the use of dimethyl-β-cyclodextrin.

The invention accordingly relates to pharmaceutical compositions for the nasal administration of the natural female sex hormones 17β-estradiol and progesterone with an increased absorption of the hormones referred to by combination with the adjuvant dimethyl-β-cyclodextrin. Examples of dosage forms of 17β-estradiol and/or progesterone suitable for nasal administration are solutions, suspensions, gels and ointments. The dosage forms containing the hormones referred to, either separately or in combination, can be used, for example, in treating or preventing postmenopausal conditions, such as vasomotor symptoms and osteoporosis.

The word progesterone, as used herein, means pregn-4-ene-3,20-dione, and comprises both progesterone obtained from natural sources and synthetic progesterone.

The word 17β-estradiol as used herein means estra-1,3,5(10)-triene-3,17β-diol, and includes both 17β-estradiol obtained from a natural source and that obtained synthetically.

According to the present invention, it was surprisingly found that 17β-estradiol and progesterone, in combination with dimethyl-β-cyclodextrin, can be nasally administered with a biological availability substantially equal to that of intravenous administration.

The following study was undertaken to study the biological availability of 17β-estradiol after nasal administration, as compared with intravenous administration. Female rabbits (New Zealanders) with an average weight of about 4 kg were used. To suppress a sternutatory reflex during nasal administration, the rabbits were lightly sedated with 0.2 ml Hypnorm ® (i.v.). The nasal administration (50 μl, unilaterally, 1 cm from the nostril) was effected by means of a small flexible polythene hose fixed to a syringe. I.v. administration (100 μl) was in the aural vein. Venous blood samples were taken from the aural vein at regular intervals to 2 hours after administration. The two nasal formulations, the i.v. formulation and the control vehicle were tested in 5 rabbits. The composition of the nasal formulations was as follows: a 0.2% 17β-estradiol suspension in Sol. benzalkonii et hypromellosi FNA and a 0.2% 17β-estradiol solution with 2% dimethyl-β-cyclodextrin in Sol. benzalkonii et hypromellosi FNA. The i.v. formulation was a 0.1% 17β-estradiol solution with 1% dimethyl-β-cyclodextrin in physiological saline. The control vehicle (placebo) was Sol. benzalkonii et hypromellosi FNA. The 17β-estradiol serum levels were analyzed by an RIA method (Pharmacia). The results are summarized in Table 1 and FIGS. 2 and 3.

$$\text{Calculation } \% \ AUC: \frac{AUC_{Fi,Kj}}{AUC_{Fiv,Kj}} \times 100\%$$

$$\text{Calculation } \% \ F: \frac{AUC_{Fi,Kj} - AUC_{Fc,Kj}}{AUC_{Fiv,Kj} - AUC_{Fc,Kj}} \times 100\%$$

$Fi$ = formul.1-4
$Fiv$ = intravenous
$Fc$ = placebo
$Kj$ = rabbit 1-5

This study shows that, after nasal administration, 17β-estradiol is rapidly and substantially completely taken up in the systemic circulation without intestinal or first-pass metabolism.

The following study was done to determine the bioavailability of progesterone after nasal administration relative to intravenous administration. Male Wistar rats, weighing 175-225 gram, were anaesthetized with Hypnorm ® (0.1 ml/100 g) intramuscularly. In order to facilitate nasal administration and to prevent peroral absorption, the trachea was canulated and the esophagus was tied to this canula. Animals were kept lying on their back on thermostated rugs (37° C.) during the experiment. Nasal formulations were instilled unilaterally through the nares using PVC-tubing affixed to a microliter syringe. The composition of the nasal formulations was as follows: a 1% progesterone suspension in Sol. benzalkonii FNA and 1% progesterone solution with 8.5% dimethyl-β-cyclodextrin in Sol. benzalkonii FNA. The intravenous formulation via a femoral vein (20 μl corresponding to 200 βg progesterone) had the same composition as the nasal progesterone/dimethyl-β-cyclodextrin solution. The control (placebo) was Sol. Benzalkonii FNA. Blood samples were taken from a canulated femoral artery at regular time intervals. Progesterone serum levels were measured using a Coat a count ® radioimmunoassay kit form DPC (Laboratorium Service, The Netherlands). In this rat model nasal administration of the described progesterone/dimethyl-β-cyclodextrin solution (20 μl corresponding to 200 μg progesterone) showed an absolute bioavailability of 58.5%±15.7% (n=5) relative to the intravenous injection, whereas the progesterone suspension (20 μl corresponding to 200 progesterone) showed an absolute bioavailability of only 18.5%±13.4% (n=4). Nasal administration of the progesterone/dimethyl-β-cyclodextrin solution gives a significantly higher progesterone absorption than the progesterone suspension (p<0.05).

A nasal formulation of 0.2% 17β-estradiol in solution with 2% dimethyl-β-cyclodextrin was given to women (n=6) with estrogen deficiency due to bilateral ovariectomy. The formulation was administered as a nasal spray in a daily dose of 0.68 mg 17β-estradiol, divided in 2 nasal gifts. Serum 17β-estradiol levels 10 min after nasal administration of 0.34 mg 17β-estradiol with this formulation were in the order of 3 nmol/l. This demonstrates a rapid and good absorption of 17β-estradiol from the described formulation. Clinical results were also encouraging. The patients decided to continue with the nasal formulation instead of oral estrogen substitution.

The composition for nasal administration according to the present invention may be of solid, semi-solid or liquid form. Preferably, it is an aqueous solution. In the case of a liquid form, the concentration of 17β-estradiol preferably ranges between 0.01% and 5% w/v and most preferably between 0.1% and 0.5% w/v. The concentration of progesterone preferably ranges from 0.05% to 5% w/v, and most preferably from 0.1% to 1% w/v. The concentration of dimethyl-β-cyclodextrin preferably ranges from 0.1% to 20% w/v and most preferably from 1% to 10% w/v.

The molar ratio of sex hormone to dimethyl-β-cyclodextrin preferably ranges from 1:6 to 4:1, and most preferably from 1:2 to 2:1.

The pH of the composition can be adjusted by adding an acid, base or buffer solution during preparation. The pH preferably ranges from 6 to 8.

Preservatives, such as benzalkonium chloride, can be added to the composition. Swelling agents, such as cellulose derivatives, can be incorporated in the composition to form nasal gels.

The solution can be autoclaved or sterilized by means of 0.2 μm membrane filtration.

The nasal compositions according to the invention have the following advantages:

1. The natural female sex hormones are rapidly and virtually completely absorbed into the systemic circulation through the nasal mucosa, without intestinal metabolism or liver first-pass effect.

2. The administration of the compositions is highly patient-friendly, which is especially important in long-term therapy.
3. Dimethyl-β-cyclodextrin is tasteless, odourless, low-toxic and little irritating to the nasal mucous membrane in the concentrations used in the composition, and accordingly is safe in long-term use.
4. The composition has no significant effect on ciliary movement in vitro, which is important, because an inhibition of ciliary movement affects the nasal defence mechanism.

The compositions according to the present invention can be prepared by dissolving 17β-estradiol and/or progesterone together with dimethyl-β-cyclodextrin in 96% alcohol, followed by evaporation at 40° C. under an N₂ stream. The dry residue can be dissolved in an aqueous medium, such as Sol. Benzalkonii FNA, whereafter, for example, sodium chloride can be added to achieve isotony.

Examples of typical compositions for the nasal administration of female sex hormones according to the present invention:

1. 100 mg 17β-estradiol was combined with 0.98 g dimethyl-β-cyclodextrin and 0.45 g sodium chloride. The total volume was made up to 50 ml with Solutio benzalkonii FNA (containing 0.01% benzalkonium chloride and 0.1% sodium edetate).
2. 250 mg progesterone was combined with 2.12 g dimethyl-β-cyclodextrin and 0.45 g sodium chloride. The total volume was made up to 50 ml with Solutio benzalkonii FNA (containing 0.01% benzalkonium chloride and 0.1% sodium edetate).
3. 100 mg 17β-estradiol and 250 mg progesterone were combined with 3.10 g dimethyl-β-cyclodextrin and 0.45 g sodium chloride. The total volume was made up to 50 ml with Solutio benzalkonii FNA (containing 0.01% benzalkonium chloride and 0.1% sodium edetate).
4. 100 mg 17β-estradiol was combined with 0.98 g dimethyl-β-cyclodextrin and 0.45 g sodium chloride. The total volume was made up to 50 ml with Solutio benzalkonii et hypromellosi FNA (containing 0.01% benzalkonium chloride and 0.1% sodium edetate and 1% methylhydroxypropyl cellulose 4000 mPa.s).

A suitable dose of the above compositions can be 0.05 ml to 0.2 ml for a single dose and 0.05 ml to 0.8 ml per 24 hours.

The compositions according to the invention are not limited to the above examples. The scope of the invention is only determined by the claims.

| BIOLOGICAL AVAILABILITY (F) IN % | | | | | | | |
|---|---|---|---|---|---|---|---|
| | $K_1$ | $K_2$ | $K_3$ | $K_4$ | $K_5$ | average | B.d. |
| O | 0 | 0 | 0 | 0 | 0 | 0 | |
| + | 100 | 100 | 100 | 100 | 100 | 100 | |
| ● | 146 | 88 | 115 | 33 | 91 | 94,6 | 41,6 |
| ▲ | 47 | 17 | 16 | 9 | 37 | 25,2 | 16 |

O control (placebo), nasal, ● 17β-estradiol, nasal, as a solution with dimethyl-β-cyclodextrin (2%), ▲ 17β-estradiol, nasal, as a suspension, + 17β-estradiol, intravenous, as a solution with dimethyl-β-cyclodextrin (1%).

Figure 1:
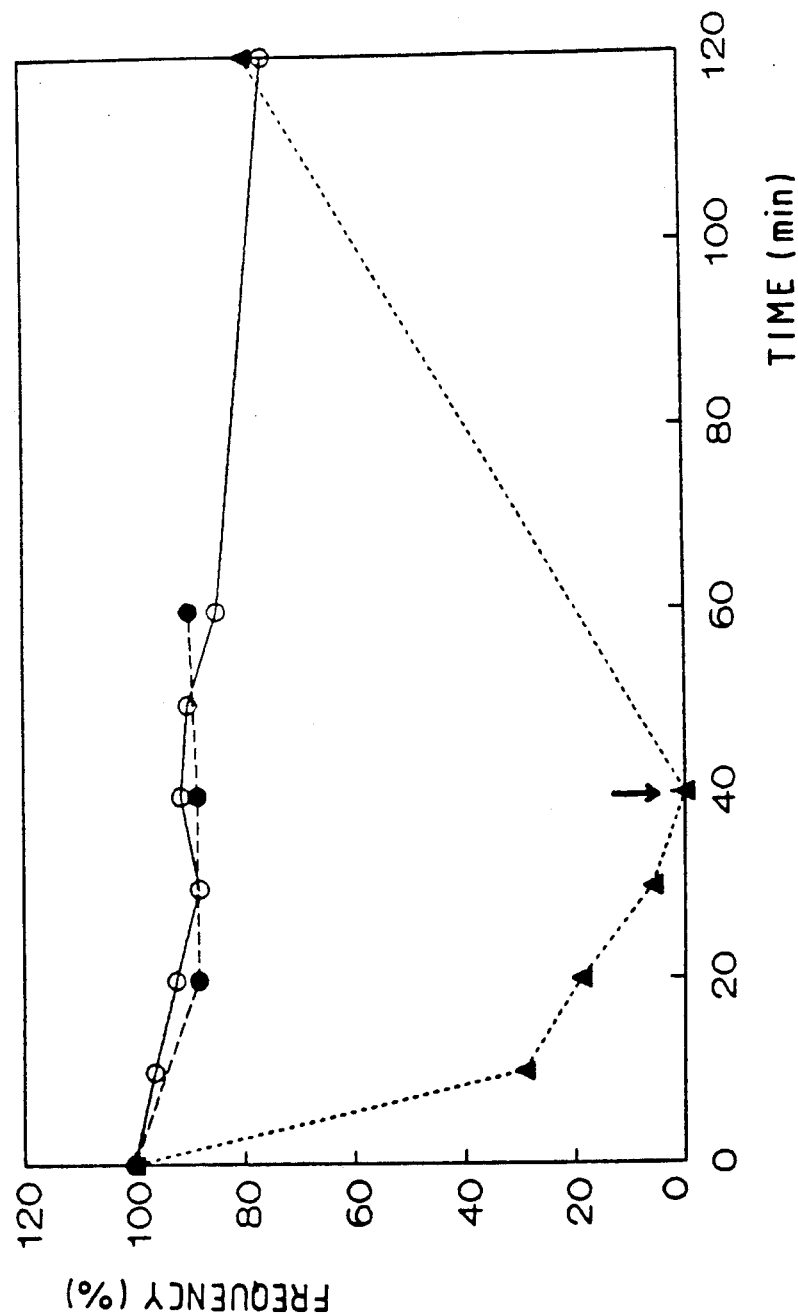
FIG. 1 shows the effect of 17β-estradiol compositions on the nasal ciliary frequency in vitro. ▲ 17β-estradiol (0.01%) in polysorbate 80 (2%), according to U.S. Pat. No. 4,383,993, O 17β-estradiol (0.1%) in dimethyl-β-cyclodextrin (1%), ● Locke Ringer (control), ↓ ciliary tissue washed in Locke Ringer.
Figure 2:
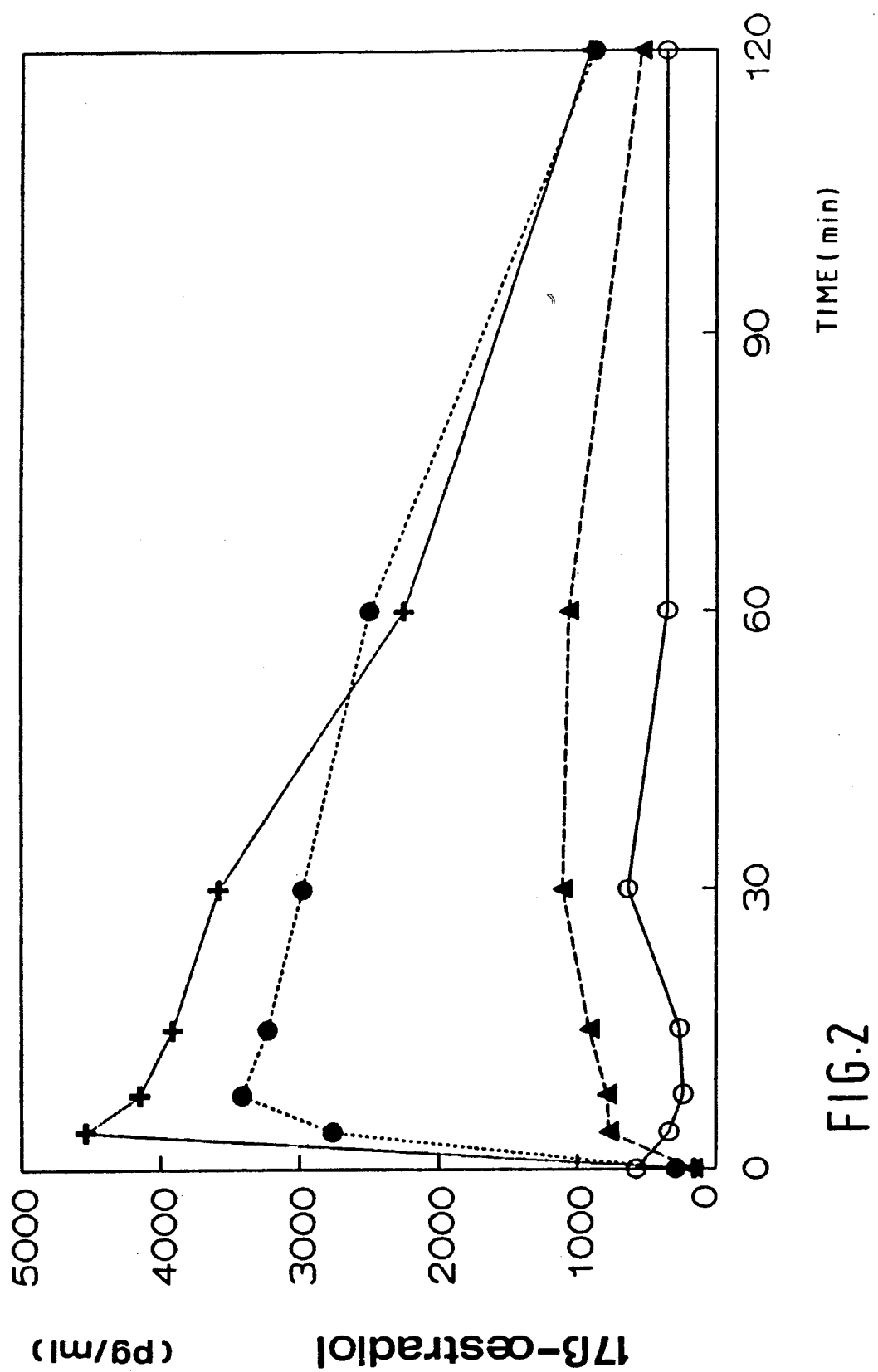
FIG. 2 shows the average serum concentration-time curves of 17β-estradiol in rabbits (n=5) after nasal and i.v. administration. O control (placebo), nasal, ● 100 μg 17β-estradiol, nasal, as a solution with dimethyl-β-cyclodextrin (2%), ▲ 100 μg 17β-estradiol, nasal, as a suspension, +100 μg 17β-estradiol, intravenous, as a solution with dimethyl-β-cyclodextrin (1%).
Figure 3:
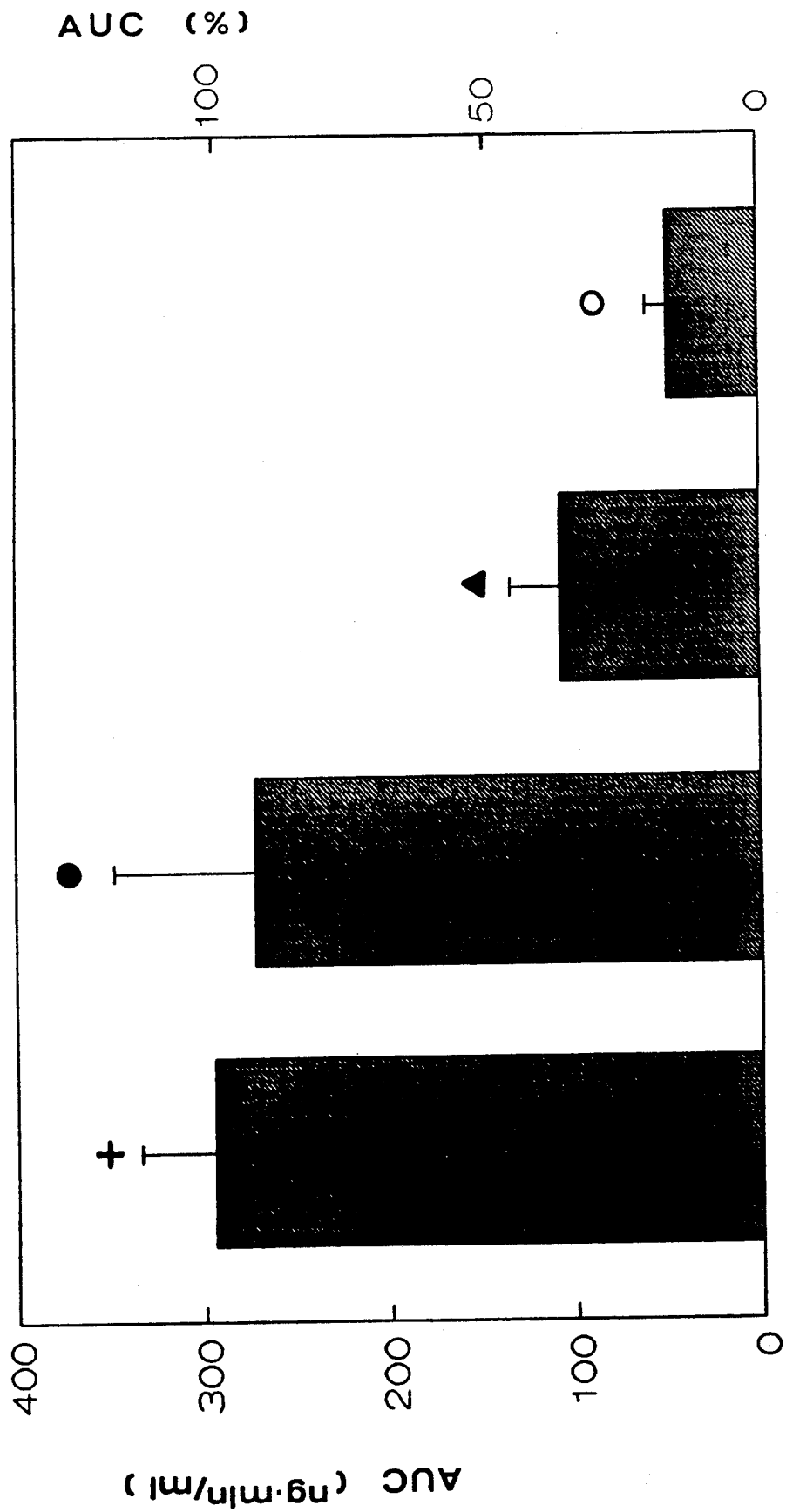
FIG. 3 shows the surfaces (AUCs) under the serum concentration-time curves after nasal and i.v. administration of 17β-estradiol. Left axis: absolute (ng.min/ml). Right axis: relative to i.v. (=100%). O control (placebo), nasal, ● 17β-estradiol, nasal, as a solution with dimethyl-β-cyclodextrin (2%), ▲ 17β-estradiol, nasal, as a suspension, +17β-estradiol, intravenous, as a solution with dimethyl-β-cyclodextrin (1%).

We claim:

1. A pharmaceutical composition suitable for the nasal administration of the human female sex hormone 17β-estradiol or the sex hormones 17β-estradiol and progesterone to a woman comprising at least 0.1% (w/v) of said sex hormone and a nasal absorption enhancing amount of dimethyl-β-cyclodextrin.
2. A pharmaceutical composition in accordance with claim 1 wherein said composition contains dimethyl-β-cyclodextrin in the amount 0.25-6 moles per mole of said sex hormone.
3. A pharmaceutical composition in accordance with claim 2 wherein said composition contains dimethyl-β-cyclodextrin in the amount 0.5-2 moles per mole of said sex hormone.
4. A pharmaceutical composition in accordance with claim 1 wherein said composition further comprises a preservative.
5. A pharmaceutical composition in accordance with claim 4 wherein said preservative is benzalkonium chloride.
6. A pharmaceutical composition in accordance with claim 1 wherein said composition further comprises an isotonicity agent.
7. A pharmaceutical composition in accordance with claim 6 wherein said isotonicity agent is sodium chloride.
8. A pharmaceutical composition in accordance with claim 1 wherein said composition further comprises a complexing agent.
9. A pharmaceutical composition in accordance with claim 8 wherein said complexing agent is sodium edetate.
10. A pharmaceutical composition in accordance with claim 1 wherein said composition further comprises a swelling agent.
11. A pharmaceutical composition in accordance with claim 10 wherein said swelling agent is methylhydroxypropyl cellulose.
12. A pharmaceutical composition in accordance with claim 1 wherein said composition is an aqueous solution comprising 0.1-20% (w/v) dimethyl-β-cyclodextrin and 0.1-0.5% (w/v) 17β-estradiol.
13. A pharmaceutical composition in accordance with claim 12 wherein said composition is an aqueous solution which comprises 1-10% (w/v) dimethyl-β-cyclodextrin and 0.1-0.5% (w/v) 17β-estradiol.
14. A pharmaceutical composition in accordance with claim 1 wherein said composition is an aqueous solution which comprises 1-10% (w/v dimethyl-β- cyclodextrin, 0.1–0.5% (w/v) 17β-estradiol and 0.1–1% progesterone.

15. A method for the nasal administration of the human female sex hormone 17β-estradiol or the sex hormones 17β-estradiol and progesterone to a woman which comprises nasally administering thereto a pharmaceutical composition comprising at least 0.1% (w/v) of said sex hormone and a nasal absorption enhancing amount of dimethyl-β-cyclodextrin.

16. A method in accordance with claim 15 wherein said composition comprises dimethyl-β-cyclodextrin in the amount 0.25–6 moles per mole of said sex hormone.

17. A method in accordance with claim 15 wherein said composition comprises dimethyl-β-cyclodextrin in the amount 0.5 to 2 moles per mole of said sex hormone.

18. A method in accordance with claim 15 wherein said composition further comprises a preservative.

19. A method in accordance with claim 18 wherein said preservative is benzalkonium chloride.

20. A method in accordance with claim 15 wherein said composition further comprises a isotonicity agent.

21. A method in accordance with claim 20 wherein said isotonicity agent is sodium chloride.

22. A method in accordance with claim 15 wherein said composition further comprises a complexing agent.

23. A method in accordance with claim 22 wherein said complexing agent is sodium edetate.

24. A method in accordance with claim 15 wherein said composition further comprises a swelling agent.

25. A method in accordance with claim 24 wherein said swelling agent is methylhydroxypropyl cellulose.

26. A method in accordance with claim 15 wherein said composition is an aqueous solution comprising 0.1–20% (w/v) dimethyl-β-cyclodextrin and 0.1–0.5% (w/v) 17β-estradiol.

27. A method in accordance with claim 15 wherein said composition is an aqueous composition comprising 0.1–20% (w/v) dimethyl-β-cyclodextrin, 0.1–0.5% (w/v) 17β-estradiol and 0.1–1% (w/v) progesterone.

28. A method in accordance with claim 15 wherein said composition is an aqueous solution comprising 1–10% (w/v) dimethyl-β-cyclodextrin and 0.1–0.5% (w/v) 17β-estradiol.

29. A method in accordance with claim 15 wherein said composition is an aqueous solution comprising 1–10% (w/v) dimethyl-β-cyclodextrin, 0.1–0.5% (w/v) 17β-estradiol and 0.1–1% (w/v) progesterone.

30. A pharmaceutical composition in accordance with claim 1 wherein said composition is an aqueous solution comprising 0.1–20% (w/v) dimethyl-β-cyclodextrin, 0.1–0.5% (w/v) 17β-estradiol and 0.1–1% (w/v) progesterone.

* * * * *